United States Patent [19]

Ringwald

[11] 4,329,354

[45] May 11, 1982

[54] THIAZOLINE AND IMIDAZOLINE DERIVATIVES USEFUL AS ANTIDEPRESSANTS

[75] Inventor: Erwin Ringwald, Riehen, Switzerland

[73] Assignee: Sandoz Ltd., Basel, Switzerland

[21] Appl. No.: 152,713

[22] Filed: May 23, 1980

[30]     Foreign Application Priority Data

Jun. 1, 1979 [GB]  United Kingdom ............... 19264/79
Jun. 1, 1979 [GB]  United Kingdom ............... 19265/79

[51] Int. Cl.³ .......................................... A61K 31/425
[52] U.S. Cl. .................................................. 424/270
[58] Field of Search ......................................... 424/270

[56]     References Cited

U.S. PATENT DOCUMENTS 2,992,232  7/1961  Bloom ............................. 260/330.5
3,499,083  3/1970  Levitt ............................. 424/246
4,159,335  6/1979  Neustadt .......................... 424/270

OTHER PUBLICATIONS

Nervenarzt, 48 (355–358) (1977).
Nervenarzt, 50 (806–808) (1979).

*Primary Examiner*—Stanley J. Friedman
*Attorney, Agent, or Firm*—Gerald D. Sharkin; Robert S. Honor; Joseph J. Borovian

[57]     ABSTRACT

This invention provides a new antidepressive use of thiazoline and imidazoline derivatives and novel pharmaceutical compositions for such use.

8 Claims, No Drawings

THIAZOLINE AND IMIDAZOLINE DERIVATIVES USEFUL AS ANTIDEPRESSANTS

The present invention relates to a novel pharmaceutical use of compounds of formula I,

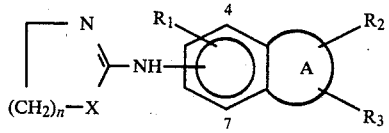

wherein
X is sulphur or imino,
n is 1 or 2,
R₁ is hydrogen, halogen, alkyl(C₁₋₄), alkylthio(C₁₋₄), alkoxy(C₁₋₄), trifluoromethyl or hydroxy,
A is a five-membered heterocyclic ring containing at least one heteroatom chosen from nitrogen, oxygen and sulphur and having 2 adjacent carbon atoms common with the benzene ring, with the proviso that the nucleus is other than benzo-2,1,3-thiadiazole, and
R₂ and R₃ are substituents which may be present in ring A, wherein
R₂ is attached to a ring carbon atom and is hydrogen, halogen, alkyl(C₁₋₄), alkoxy(C₁₋₄), alkylthio(C₁₋₄), trifluoromethyl or hydroxy and
R₃ is attached to a ring nitrogen atom and is hydrogen or alkyl(C₁₋₄),
with the proviso that, when A is [c]pyrrole, the nitrogen atom of A is substituted by alkyl(C₁₋₄),
and of compounds of formula I',

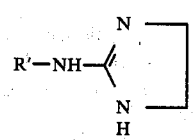

wherein either (i) R' is a radical of formula II,

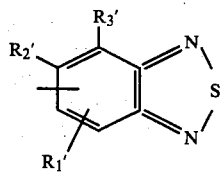

wherein each of R₁', R₂' and R₃', independently, is hydrogen, halogen, alkyl(C₁₋₄), alkoxy(C₁₋₄), nitro, cyano, hydroxy or alkylthio(C₁₋₄), or (ii) R' is a radical of formula III,

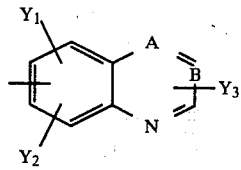

wherein either
each of A and B is =CH—, or one of A and B is =CH— and the other of A and B is =N—, Y₁ and Y₂, independently, are hydrogen, halogen, alkyl(C₁₋₄), alkoxy(C₁₋₄), nitro, trifluoromethyl, cyano, hydroxy or alkylthio(C₁₋₄), and
Y₃ is hydrogen, alkyl(C₁₋₄) or alkoxy(C₁₋₄).

The compounds of formula I are in general known, e.g. from DOS No. 2 800 062, U.S. Pat. No. 4,086,353 and U.K. Pat. No. 1,466,924. The compounds have been stated to have diverse pharmacological activities, e.g. myotonolytic activity. The compounds of formula I', wherein R' is a radical of formula II are also in general known. They are disclosed in U.S. Pat. No. 3,843,668 and U.K. Pat. No. 1,552,163 and said to be useful as anti-tremor and anti-rigor agents. The compounds of formula I', wherein R' is a radical of formula III are, in general, known e.g. from U.K. Pat. No. 1,381,979 and said to be active as antihypertensives. We have now surprisingly fount that the above compounds of formula I and I' exhibit antidepressive activity.

In the compounds of formula I A is, for example, [b] or [c]pyrrole, [d]imidazole, [d]pyrazole, [d]triazole, [b] or [c]furan, [c] or [d]isoxazole, [d]oxazole, [c]furazan, [b] or [c]thiophene, [c] or [d]isothiazole, [d]thiazole, [d](1,2,3)-thiadiazole, [b] or [c]pyrroline, [b] or [c]dihydrofuran or [b]dihydrothiophene. Preferably A is [b]furan, [b]thiophene, [d]oxazole or [d]triazole, especially [b]furan. Halogen means fluorine, chlorine, bromine or iodine, preferably bromine or chlorine. Alkyl, alkoxy or alkylthio preferably contains 2 carbon atoms, especially 1 carbon atom. R₁ is preferably other than hydroxy and is preferably hydrogen, chlorine or methyl. R₁ is preferably ortho to the heterocyclic-amino moiety. R₂ is preferably alkyl, hydrogen or halogen, especially chlorine. The heterocyclic-amino residue is preferably attached to position 4 to 7 of the bicyclic moiety. When the heterocyclic-amino moiety is attached to the 4 position of the bicyclic moiety, then R₂, when present, is preferably in the 3 position. R₂, when present, is preferably alkyl, n is preferably 1.

Examples of compounds of formula I are: 4-methyl-5-(2-thiazolin-2-yl-amino)-indazole, and 4-chloro-5-(2-thiazolin-2-yl-amino)-indazole.

In the compounds of formula I' any carbon containing substituent has especially 1 carbon atom.

Halogen is preferably fluorine, chlorine or bromine.

Preferred examples of formula I', where R' is a radical of formula II, are those of formula I'a,

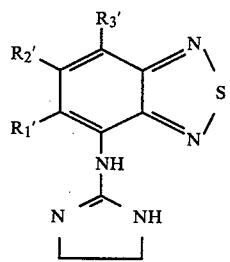

wherein each of R₁', R₂' and R₃', independently, is hydrogen, halogen, alkyl(C₁₋₄), alkoxy(C₁₋₄), nitro, cyano, hydroxy or alkylthio(C₁₋₄), and especially 5-chloro-4-(2-imidazolin-2-yl-amino)-2,1,3-benzothiadiazole.

Preferred example of formula I', where R' is a radical of formula III, are those compounds wherein Y₁ is halogen, especially chlorine or bromine, and Y₂ and Y₃ are hydrogen, e.g. 5-bromo- and 5-chloro-6-(2-imidazolin- 2-yl-amino)-quinolines and -quinoxalines and 8bromo-7-(2imidazolin-2-yl-amino)-quinazoline and -quinoline.

The antidepressive activity of the compounds is indicated in clinical trials with subjects suffering from somatogenic, endogenous and psychogenic depressions and in standard animal tests. For example in double-blind clinical trials, 5-chloro-4-(2-imidazolin-2-yl-amino)-2,1,3-benzothiadiazole was administered to 38 subjects with somatogenic depressions and suffering from multiple sclerosis at a daily dose of from 4 to 12 mg p.o. in divided doses 2 to 4 times a day. A distinct and rapid elevation of mood was observed within 6 weeks in over 85% of the subjects as determined by standard rating scales, e.g. Hamilton or the brief psychiatric rating scale (BPRS). This improvement in mood was unexpectedly more pronounced and quicker than the improvement in the multiple sclerosis symptoms. This indicates a genuine anti-depressant effect.

Other clinical trials have confirmed that 5-chloro-4-(2-imidazolin-2-ylamino)-2,1,3-benzothiadiazole at a dose of from 6 to 30 mg daily p.o. elevates the mood in depressed patients and has an antidepressant effect according to standard rating scales over 40 days. Moreover 5-chloro-4-(2-imidazolin-2-ylamino)-2,1,3-benzothiadiazole at a daily dose of 3 to 6 mg p.o. in divided doses 2 to 4 times a day to about 60 subjects leads within 2 weeks to a significant anxiolytic effect in 60-70% of the subjects in 50% of the subjects to a C.N.S. stimulating effect. These effects also with the mood elevating effect contribute to the anti-depressant action of 5-chloro-4-(2-imidazolin-2-ylamino)-2,1,3-benzothiadiazole in psychogenic depressions.

The antidepressive activity of the compounds is confirmed in standard animal tests, for example, by an inhibition of tetrabenazine-induced catalepsy and ptosis in rats on intraperitoneal administration of from 5 to 20 mg/kg animal body weight of the compound in accordance with the method described by Stille (Arzneimittel-Forsch. 1964, 14, 534). Furthermore, the compounds on administration of from 1 to 30 mg/kg i.p. to mice reduce the immobility induced by water-immersion according to the method described by R. D. Porsolt et al., Arch. int. Pharmacodyn. 229, 327–336 (1977).

The above compounds are therefore useful as antidepressants, e.g. for the treatment of somatogenic, endogenous and psychogenous depressions.

For the above mentioned novel use the dosage will, of course, vary depending on the compound employed, mode of administration and therapy desired. However, in general, satisfactory results are obtained with a daily dosage of from about 0.01 mg to about 30 mg per kg animal body weight, conveniently given in divided doses 2 to 4 times a day or in sustained release form. For the larger mammal, the total daily dosage is in the range from about 3 mg to about 50 mg, e.g. 30 to 50 mg. 3 to 30 mg is indicated in the case of somatogenic depressions. The dose is conveniently administered in divided doses 2 to 4 times a day in unit dosage form containing from about 1 mg to about 25 mg of the compound admixed with a solid or liquid pharmaceutical carrier or diluent.

It is to be appreciated that the compound may have to be administered for at least 4 weeks before a significant anti-depressant effect is observed.

For 5-chloro-4-(2-imidazolin-2-yl-amino)-2,1,3-benzothiadiazole an example of the total daily dosage is from 6 to 30 mg, conveniently administered in unit dosage form containing from about 3 to about 15 mg of the compound.

The compounds may be administered in free base form or in pharmaceutically acceptable acid addition salt form. Such salt forms are known and include for example the hydrochloride. The free base forms and said acid addition salt forms exhibit the same order of activity.

The compounds may be administered orally as pharmaceutical compositions in the form of tablets, powders, granules, capsules, suspensions, sirups and elixirs, or parenterally in the form of injectable solutions or suspensions. Aside from the compound of formula I or I' the compositions may contain pharmaceutically inert organic or inorganic adjuvants, optionally granulating agents, binding agents, lubricants, dispersing agents, wetting agents and preservatives. Moreover, the pharmaceutical compositions may contain colouring, flavouring and sweetening substances, etc. Adjuvants for the production of tablets may be calcium carbonate, lactose, microcrystalline cellulose, mannitol, or talc. Starch and alginic acid or microcrystalline cellulose may be used as granulating and disintegrating agents, starch, polyvinylpyrrolidone and gelatine may be used as binding agents, and magnesium stearate, stearic acid, colloidal silicon dioxide and talc as lubricants. Tablet formulations may be coated or uncoated, with the coating being applied in manner per se and having the purpose of delaying the disintegration and adsorption in the gastrointestinal tract, thus providing a retarded effect over a longer period. Suitable suspending agents for the production of liquid administration forms are especially methyl cellulose, tragacanth and sodium alginate. Suitable wetting agents are e.g. polyoxyethylene stearate and polyoxyethylene sorbitan-monooleate. Furthermore, preservatives such as p-hydroxy-benzoic acid alkyl ester may be used. Capsule formulations may contain the compound of formula I and I' on its own or together with an inert solid diluent, for example, calcium phosphate, starch, lactose, mannitol, colloidal silicon dioxide and microcrystalline cellulose.

Solid preparations are preferred, especially hard-filled capsules and tablets, for reasons of easier production and favourable administration.

The invention also provides a pack containing a pharmaceutical composition containing a compound of formula I or I' together with instructions for use as an antidepressive agent. The compound may be in form of solid unit dosage forms, e.g. in a blister pack made from metal or plastic foil.

The following Examples are illustrative of compositions for use in the invention.

EXAMPLE 1

Tablet suitable for oral administration

Tablets containing the ingredients indicated below may be prepared by conventional granulating techniques and are administered at a dose of one or two tablets three to four times a day.

| Ingredient | Weight (mg) |
| --- | --- |
| 5-chloro-4-(2-imidazolin-2-yl-amino)-2,1,3-benzothiadiazole hydrochloride (active agent) | 4.576 mg (= 4.0 mg base) |
| Lactose | 110.0 mg |
| Microcrystalline cellulose | 101.024 mg |
| Colloidal silicon dioxide | 0.4 mg |

| Ingredient | Weight (mg) |
| --- | --- |
| Stearic acid | 4.0 mg |
| | 220.000 mg |

If desired, the tablet may be shaped so that it may be easily divided into two.

EXAMPLE 2

Capsule suitable for oral administration

Capsules containing the ingredients indicated below may be prepared by conventional techniques and are administered at a dose of one capsule two to four times a day.

| Ingredient | Weight (mg) |
| --- | --- |
| 5-chloro-4-(2-imidazolin-2-yl-amino)-2,1,3-benzothiadiazole hydrochloride | 1.144 mg ($\cong$ 1 mg base) |
| Lactose | 174.356 mg |
| Corn starch | 120.0 mg |
| Colloidal silicon dioxide | 1.5 mg |
| Magnesium stearate | 3.0 mg |
| | 300.0 mg |

EXAMPLE 3

Sterile solution for injection

A solution for injection containing the ingredients indicated below may be prepared by conventional techniques including buffering as indicated below and subsequent sterilizing in conventional manner. The solution may be injected twice a day.

| Ingredient | Weight/Volume |
| --- | --- |
| 5-chloro-4-(2-imidazolin-2-yl-amino)-2,1,3-benzothiadiazole hydrochloride (active agent) | 3.432 mg/ml* ($\sim$ 3.0 mg base) |
| Sodium chloride | 7.000 mg/ml |
| Acetic acid conc. | 0.950 mg/ml |
| Sodium acetate trihydrate | 2.380 mg/ml |
| Distilled water | to 1 ml |
| Buffer to pH 5 | |

*may be replaced by 0.572 or 6.864 mg of active agent

If desired the solution may be sealed into ampoules under carbon dioxide.

What we claim is:

1. A method of treating depression which comprises administering to a subject in need of such treatment a therapeutically effective amount of a compound of formula I'a

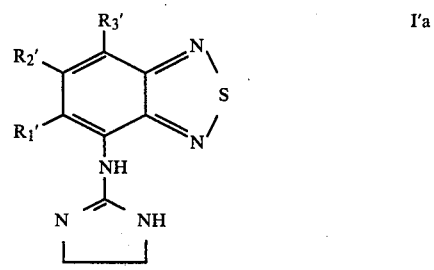

wherein each of $R_1'$, $R_2'$ and $R_3'$, independently, is hydrogen, halo, $C_{1-4}$ alkyl, $C_{1-4}$ alkoxy, nitro, cyano, hydroxy or $C_{1-4}$ alkylthio, said compound being in free base or in pharmaceutically acceptable acid addition salt form.

2. A method according to claim 1 wherein the depression is a somatogenic depression.

3. A method according to claim 1 wherein the depression is an endogenous depression.

4. A method according to claim 1 wherein the depression is a psychogenous depression.

5. A method according to claim 1 wherein the compound is 5-chloro-4-(2-imidazolin-2-yl-amino)-2,1,3-benzothiadiazole.

6. A method according to claim 1 wherein the compound is administered at a daily dosage of from 6 to 30 mg.

7. A method according to claim 1 wherein the compound is administered at a daily dosage of from 30 to 50 mg.

8. A method according to claim 6 wherein the compound is administered in unit dosage form containing from about 3 to about 15 mg of the compound.

* * * * *